(12) United States Patent
Parthasarathy et al.

(10) Patent No.: US 11,007,382 B2
(45) Date of Patent: May 18, 2021

(54) REAL TIME DOSIMETRY OF ULTRASOUND IMAGING PROBE

(71) Applicant: KONINKLIJKE PHILIPS N.V., Eindhoven (NL)

(72) Inventors: Vijay Parthasarathy, Andover, MA (US); Andrew Lee Robinson, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 207 days.

(21) Appl. No.: 16/099,748

(22) PCT Filed: Jun. 19, 2017

(86) PCT No.: PCT/EP2017/064859
§ 371 (c)(1),
(2) Date: Nov. 8, 2018

(87) PCT Pub. No.: WO2018/001760
PCT Pub. Date: Jan. 4, 2018

(65) Prior Publication Data
US 2019/0151682 A1 May 23, 2019

Related U.S. Application Data

(60) Provisional application No. 62/356,177, filed on Jun. 29, 2016.

(51) Int. Cl.
*A61N 5/10* (2006.01)
*A61B 8/00* (2006.01)

(52) U.S. Cl.
CPC .......... *A61N 5/1049* (2013.01); *A61B 8/4218* (2013.01); *A61B 8/4444* (2013.01);
(Continued)

(58) Field of Classification Search
CPC .... A61N 2005/1058; A61N 2005/1094; A61N 5/1071
See application file for complete search history.

(56) References Cited

U.S. PATENT DOCUMENTS 7,831,016 B2 11/2010 Saoudi et al.
8,831,708 B2 9/2014 Paladini
(Continued)

OTHER PUBLICATIONS

Carrara, M. et al., "In vivo rectal wall measurements during HDR prostate brachytherapy with MOSkin dosimeters integrated on a trans-rectal US probe: Comparison with planned and reconstructed doses". Radiotherapy and Oncology, vol. 118, Issue 1, Jan. 2016, pp. 148-153.
(Continued)

*Primary Examiner* — Christine H Matthews (57) ABSTRACT

An ultrasound probe includes an ultrasound probe housing and one or more ultrasound transducers disposed in the ultrasound probe housing. A dosimeter or ionizing radiation detector is disposed in or attached to the ultrasound probe housing. An alarm device receives radiation dose or radiation exposure data acquired by the dosimeter or ionizing radiation detector. The alarm device includes an electronic processor programmed to detect excessive radiation dose or radiation exposure received by the ultrasound probe based on the radiation dose or radiation exposure data acquired by the dosimeter or ionizing radiation detector, and output an alarm warning of the detection of excessive radiation dose or radiation exposure received by the ultrasound probe. In some embodiments, the dosimeter is a one-time use dosimeter that is not resettable.

14 Claims, 4 Drawing Sheets

(52) U.S. Cl.
CPC .......... *A61B 8/4472* (2013.01); *A61B 8/4483* (2013.01); *A61N 5/1071* (2013.01); *A61N 2005/1058* (2013.01); *A61N 2005/1087* (2013.01); *A61N 2005/1089* (2013.01); *A61N 2005/1094* (2013.01); *A61N 2005/1095* (2013.01)

(56) References Cited

U.S. PATENT DOCUMENTS

| | | |
|---|---|---|
| 2005/0251029 A1 | 11/2005 | Khamene et al. |
| 2011/0160589 A1 | 6/2011 | Fu et al. |
| 2012/0230574 A1 | 9/2012 | Rozenfeld et al. |
| 2013/0033700 A1 | 2/2013 | Hallil |
| 2017/0014643 A1 | 1/2017 | Wirtz et al. |
| 2017/0165504 A1 | 6/2017 | Dollinger et al. |

OTHER PUBLICATIONS

Schlosser, J.K. et al., "Telerobotic system concept for real-time soft-tissue imaging during radiotherapy beam delivery." Medical Physics, 2010. 37(12): p. 6357.

FIG. 4

REAL TIME DOSIMETRY OF ULTRASOUND IMAGING PROBE

CROSS-REFERENCE TO PRIOR APPLICATIONS

This application is the U.S. National Phase application under 35 U.S.C. § 371 of International Application Serial No. PCT/EP2017/064859, filed on Jun. 19, 2017, which claims the benefit of U.S. Patent Application No. 62/356,177, filed on Jun. 29, 2016. This application is hereby incorporated by reference herein.

FIELD

The following relates generally to the external beam radiation therapy (EBRT) arts, ultrasound procedure monitoring arts, and the like.

BACKGROUND

External Beam Radiation Therapy (EBRT) employs an ionizing radiation beam as an oncological treatment tool. The ionizing radiation may be an electron beam, a proton beam, an x-ray beam, or the like. EBRT is commonly delivered as a fractionated therapy that involves multiple stages, beginning with pre-treatment imaging, followed by image-based treatment planning and culminating in multi-fraction treatment delivery. Each fraction is delivered on a separate day.

A difficulty with fractionated EBRT is that the target tumor and/or radiation-sensitive critical organs may shift between treatment delivery fractions (inter-fraction motion), or even during a single treatment delivery fraction (intra-fraction motion). Monitoring such motion is problematic, especially in the case of intra-fractional motion, because monitoring devices can be damaged by exposure to the ionizing radiation used in the therapy. Laser-based techniques have been developed to account for global patient shifts prior to delivering each fraction, but may be ineffective for detection motion of internal organs, or of the target tumor. Intermittent imaging by an imaging modality such as cone beam computed tomography (CBCT) may be used to account for inter-fractional motion, but is difficult or impossible to employ during a radiation therapy treatment delivery fraction to detect intra-fraction motion.

Another known approach for monitoring a radiation therapy treatment session (i.e. fraction) is ultrasound (US) imaging, which has good discrimination for soft tissue targets of the type that usually make up the malignant tumor and neighboring critical organs. However, the use of US imaging during a treatment delivery fraction has certain difficulties. A sonographer generally cannot be present to position the US probe due to the risk of radiation exposure; accordingly, either the US probe is stationary throughout the radiation therapy session, or a robotic US probe manipulator is used to manipulate the US probe. Furthermore, the US probe should not be irradiated by the therapeutic ionizing radiation beam during the radiation therapy session, which requires careful positioning of the US probe.

The following discloses a new and improved systems and methods that address the above referenced issues, and others.

SUMMARY

In one disclosed aspect, an ultrasound probe includes an ultrasound probe housing, one or more ultrasound transducers disposed in the ultrasound probe housing, and a dosimeter or ionizing radiation detector disposed in or attached to the ultrasound probe housing. An alarm or monitoring device is configured to receive radiation dose or radiation exposure data acquired by the dosimeter or ionizing radiation detector. The alarm or monitoring device includes an electronic processor programmed to (i) detect excessive radiation dose or radiation exposure received by the ultrasound probe based on the radiation dose or radiation exposure data acquired by the dosimeter or ionizing radiation detector and (ii) output an alarm warning of the detection of excessive radiation dose or radiation exposure received by the ultrasound probe.

In another disclosed aspect, an external beam radiation therapy device comprises a radiation therapy delivery device configured to apply an ionizing radiation beam to a subject, and an ultrasound probe as set forth in the immediately preceding paragraph configured to monitor an internal organ of the subject while the radiation therapy delivery device applies the ionizing radiation beam to the subject. The radiation therapy delivery device may, for example, be configured to apply an ionizing x-ray, electron, or proton beam to the subject.

In another disclosed aspect, an ultrasound probe comprises an ultrasound probe housing, one or more ultrasound transducers disposed in the ultrasound probe housing, and a one-time use dosimeter that is not resettable disposed in or attached to the ultrasound probe housing.

In another disclosed aspect, an external beam radiation therapy method is disclosed. Radiation therapy is performed on a subject by applying at least one ionizing radiation beam to the subject. While applying the at least one ionizing radiation beam to the subject, the subject is imaged using an ultrasound probe that is not located in the at least one ionizing radiation beam. While applying the at least one ionizing radiation beam to the subject, radiation dose or radiation exposure received by the ultrasound probe is measured using a dosimeter or ionizing radiation detector that is integral with or attached to the ultrasound probe.

One advantage resides in providing for monitoring of radiation dose received by an ultrasound probe used in monitoring radiation therapy sessions.

Another advantage resides in providing for improved quality control in timely replacement of an ultrasound probe used in monitoring radiation therapy sessions.

Another advantage resides in providing for assessing radiation exposure of an ultrasound probe used to monitor a radiation therapy session (i.e. fraction).

Another advantage resides in providing for real-time assessment of radiation exposure of an ultrasound probe during its use in monitoring a radiation therapy session.

Another advantage resides in providing for real-time assessment of radiation exposure of an ultrasound probe during its use in monitoring a radiation therapy session and for taking remedial action if the radiation exposure exceeds an acceptable level.

Another advantage resides in providing for detection of inadvertent exposure of an ultrasound probe used to monitor a radiation therapy session to the therapeutic radiation beam used in delivering the radiation therapy.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. Unless otherwise noted, the drawings are diagrammatic and are not to be construed as being to scale or to illustrate relative dimensions of different components.

DETAILED DESCRIPTION

A radiation therapy session employing an external radiation beam and including ultrasound (US) monitoring should be designed to avoid irradiating the US probe with the therapeutic ionizing radiation used to deliver the radiation therapy. This can be achieved by placing the US probe outside of the beam path but close enough to the irradiated region of the subject to provide useful US imaging.

However, it is recognized herein that is not always possible to avoid some radiation exposure of the US probe, especially in the case of multi-beam or tomographic radiation therapy in which there is not a single fixed radiation beam path. Even if the session is designed to avoid irradiating the US probe, errors can occur in placement of the US probe, placement of the patient, or other types of errors which can lead to radiation exposure of the US probe. Moreover, even if the US probe never enters the path of the radiation beam during the radiation therapy session, stray ionizing radiation may reach the US probe by way of imperfect beam collimation or beam spread, and/or scattering of radiation from beam shaping components, attenuators, or the like. Exposure of the US probe to the radiation beam can lead to radiation damage to the US probe and consequent US image artifacts or even to failure of the US probe. While stray radiation is of lower level, over time this lower-level exposure can degrade the US probe, again leading to introduction of image artifacts and/or reduced operating lifetime. These problems can be enhanced in the case of more complex US probes such as those used for three-dimensional (3D) ultrasound imaging that may include on-board (i.e. integral) electronics for operating US transducer arrays to perform spatial sweeps or other complex sonication and US readout operations.

In embodiments disclosed herein, the US probe is provided with a built-in or attached dosimeter for measuring the (cumulative) radiation dose received by the US probe. This dose information may be used in various ways. In one approach, the dosimeter reading is checked after each use of the US probe in a radiation therapy session. When the (cumulative) dose exceeds a maximum permissible dose threshold, the US probe should be replaced. This approach employs the built-in or attached dosimeter as a maintenance scheduling tool, in order to more accurately gauge the operational lifetime of the US probe. This approach can also detect a situation in which the US probe received a high dose of radiation over a single radiation therapy session (typically because the US probe was inadvertently placed in the ionizing radiation beam) since this will correspond to an unexpectedly large increase in accumulated dose over a single radiation therapy session.

In other embodiments, the built-in or attached dosimeter includes a transmitter, optionally wireless (or alternatively wired, with the transmitter connection bundled into the US probe cable), which enables real-time readout of the dose measured by the dosimeter. This approach has the advantage of enabling more rapid detection of a high radiation exposure level of the US probe due to its inadvertent positioning within the therapeutic radiation beam. This rapid detection, in turn, may enable remedial action to be taken in order to limit damage to the US probe. In one implementation, the time derivative of the dose versus time signal is monitored in real-time via the transmitter. A sharp and rapid rate of increase in cumulative dose over a short time interval indicates a high radiation exposure level, typically indicating the dosimeter has entered the main ionizing radiation beam. If this is observed then an alarm may be output indicating the high radiation situation, and the clinician performing the radiation therapy session can take appropriate remedial action. For example, the radiation beam may be shuttered and the US probe manually moved to a less-exposed position before continuing the radiation therapy. Alternatively, if the US probe is remotely controlled via a robotic apparatus, then the US probe can be moved robotically to a less-exposed position without shuttering the beam and thereby interrupting the radiation therapy session. On the other hand, if robotic control of the US probe position is not available and interruption of the radiation therapy session is contraindicated, then no immediate remedial action may be taken but the acquired US images may be marked as possibly unreliable due to high radiation exposure experienced by the US probe. Furthermore, as the dosimeter records the cumulative dose, the reading of the dosimeter after the radiation therapy session is complete can still be measured to inform the clinician as to whether the US probe received a sufficiently high cumulative dose over the session to require its immediate replacement.

A dosimeter measures the radiation dose, that is, the cumulative amount of radiation received by the US probe. The radiation dose is of interest for assessing the remaining (reliable) operational lifetime of the US probe and, as noted above, the radiation dose can be used to assess radiation exposure level as a function of time by taking the time derivative of the radiation dose. The dosimeter may be a one-time use dosimeter which is discarded after the cumulative dose reaches the threshold, or may be a resettable device in which the dosimeter reading can be reset to zero to enable reuse of the dosimeter for monitoring radiation dose absorbed by successive US probes.

In one preferred embodiment for use in maintenance/quality control, a non-resettable one-time use dosimeter is integrated into the US probe, e.g. disposed inside its housing or permanently secured to the outside of the US probe in a non-removable fashion. As the dosimeter cannot be reset or removed from the US probe, it provides a reliable measure of the cumulative dose received by the US probe over its lifetime. Accordingly, it can be used as a reliable gauge for setting regulatory standards, e.g. the US probe must be replaced when the integral non-resettable one-time use dosimeter indicates the cumulative dose received by the US probe exceeds a maximum dose prescribed by applicable governmental, medical institutional, and/or other regulation.

In some embodiments, it is contemplated to substitute an ionizing radiation detector for the dosimeter. An ionizing radiation detector measures current radiation exposure, rather than the radiation dose accumulated over time. When using an ionizing radiation detector, the radiation dose can be obtained from the radiation exposure measured by the ionizing radiation detector via time-integration of the radiation exposure. An ionizing radiation detector may be preferable for embodiments employing a transmitter in which the real-time radiation exposure level is of interest, e.g. to provide feedback for real-time robotic adjustment of the probe position to reduce excessive radiation exposure.

Further disclosure is provided by way of the illustrative embodiments which are described next.

Figure 1:
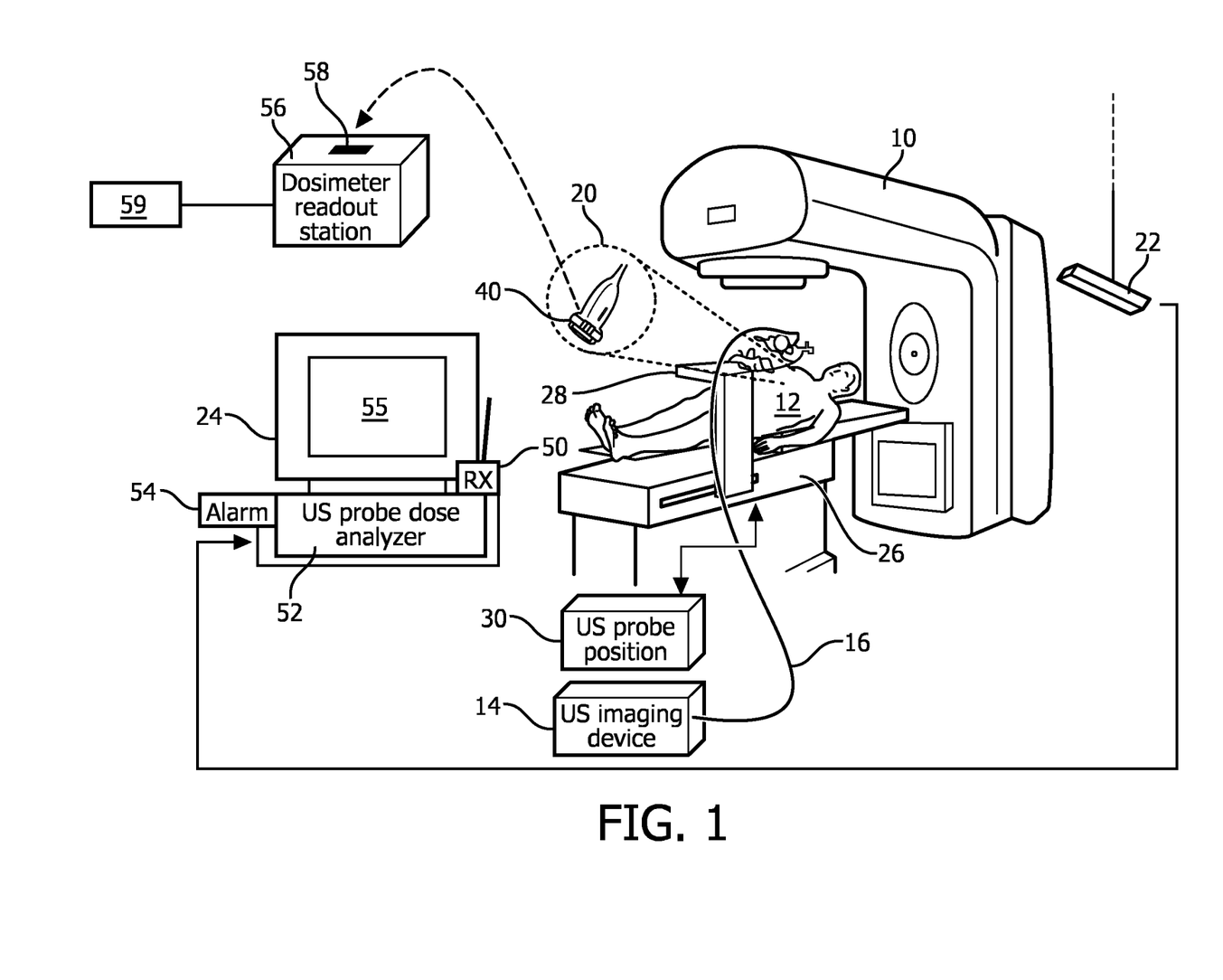
FIG. 1 diagrammatically shows a radiation therapy system including an illustrative ionizing radiation beam source (illustrative linac) and an illustrative ultrasound imaging device with an illustrative robotically movable ultrasound probe.

With reference to FIG. 1, an illustrative external beam radiation therapy (EBRT) device includes a radiation therapy delivery device 10 configured to apply an ionizing radiation beam to a subject 12 (typically a human oncology patient, although in a veterinary setting the subject could be a dog, cat or other animal receiving oncology care). The illustrative radiation therapy delivery device 10 is a linear accelerator (linac) that applies an ionizing radiation beam in the form of an accelerated electron beam. In other exemplary embodiments the ionizing radiation beam may be an accelerated proton beam (i.e. proton beam therapy) or a high-energy ionizing x-ray beam. In the illustrative embodiment, the radiation therapy is performed on the subject 12 by applying a single ionizing (i.e. accelerated electron) radiation beam to the subject; however, in multi-beam systems more than one ionizing radiation beam may be applied simultaneously; in tomographic embodiments, the ionizing radiation beam is revolved around the patient. In some embodiments, the performed radiation therapy is intensity-modulated radiation therapy (IMRT) in which a multi-leaf collimator (MLC) is used to shape the cross-sectional profile of each radiation beam to deliver an accumulated dose that closely conforms with the shape of the malignant tumor or region that is the target of the radiation therapy. These are merely illustrative examples of some illustrative radiation therapy procedures.

While applying the at least one ionizing radiation beam to the subject 12, the subject 12 is imaged using an ultrasound (US) imaging device 14 and a connected (by illustrative cable 16) ultrasound (US) probe 20. Note that for illustrative convenience FIG. 1 shows the US probe 20 in an enlarged inset. The US probe 20 is not intended to be located in the at least one ionizing radiation beam, and in the illustrative embodiment is located externally of the subject 12, that is, not inserted into any body cavity of the subject 12. (In other embodiments, it is contemplated to have the US probe disposed in a body cavity if such positioning provides a good vantage point for imaging the internal organs of interest and does not introduce substantial medical risk or patient discomfort, and is designed to not place the US probe into the path of the ionizing radiation beam). The imaging provided by the US imaging device 14 and connected US probe 20 may be used for various purposes, such as verifying the anatomical configuration expected based on earlier-acquired planning images, initial positioning of the subject 12, and/or detecting intra-fractional motion of the target tumor and/or organs of risk. Intra-fractional motion can be caused by diverse sources, such as shifting of fluid in a bladder, volitional movement by the patient, non-volitional movement due to autonomous or semi-autonomous physiological systems (e.g. respiration, cardiac cycling), or so forth. In some embodiments, this information is stored and made available to medical personnel to assess the impact (if any) of such detected motion on the efficacy of the radiation therapy and/or potential radiation damage to critical anatomy neighboring the target region. Additionally or alternatively, remedial action may be taken during the radiation therapy fraction to compensate for the motion, e.g. by adjusting the radiation beam parameters, re-positioning the subject 12, or so forth. In some cases, the intra-fractional motion may be sufficient to dictate early termination of the radiation delivery in the interest of patient safety.

In embodiments in which the US imaging is used to provide US guidance for adjusting the radiation therapy procedure, a tracking device 22 may be provided to track the position of the subject 12 in a reference frame associable with the reference frame of the US imaging. For example, the tracking device 22 may be an electromagnetic (EM) or optical tracking device employing a reference sensor (not shown) disposed on the US probe 20 or on some other component spatially relatable to the US imaging frame of reference. A computer 24 or other electronic data processing device including an electronic processor (e.g. microprocessor or microcontroller) receives data from the US imaging device 14 and from the tracking device 22 and is programmed to perform one or more guidance operations, such as adjusting ionizing radiation beam parameter(s), automatically re-positioning the patient using a motorized patient couch 26 or providing instructions for manually re-positioning the patient, and/or so forth. In some embodiments, the US probe 20 is remotely positioned (and/or re-positioned) by operation of a robot 28, and the control computer 24 may provide a user interface via which medical personnel may operate an US positioning controller 30 to control the robot 28 to (re-)position the US probe 20.

Figure 2:
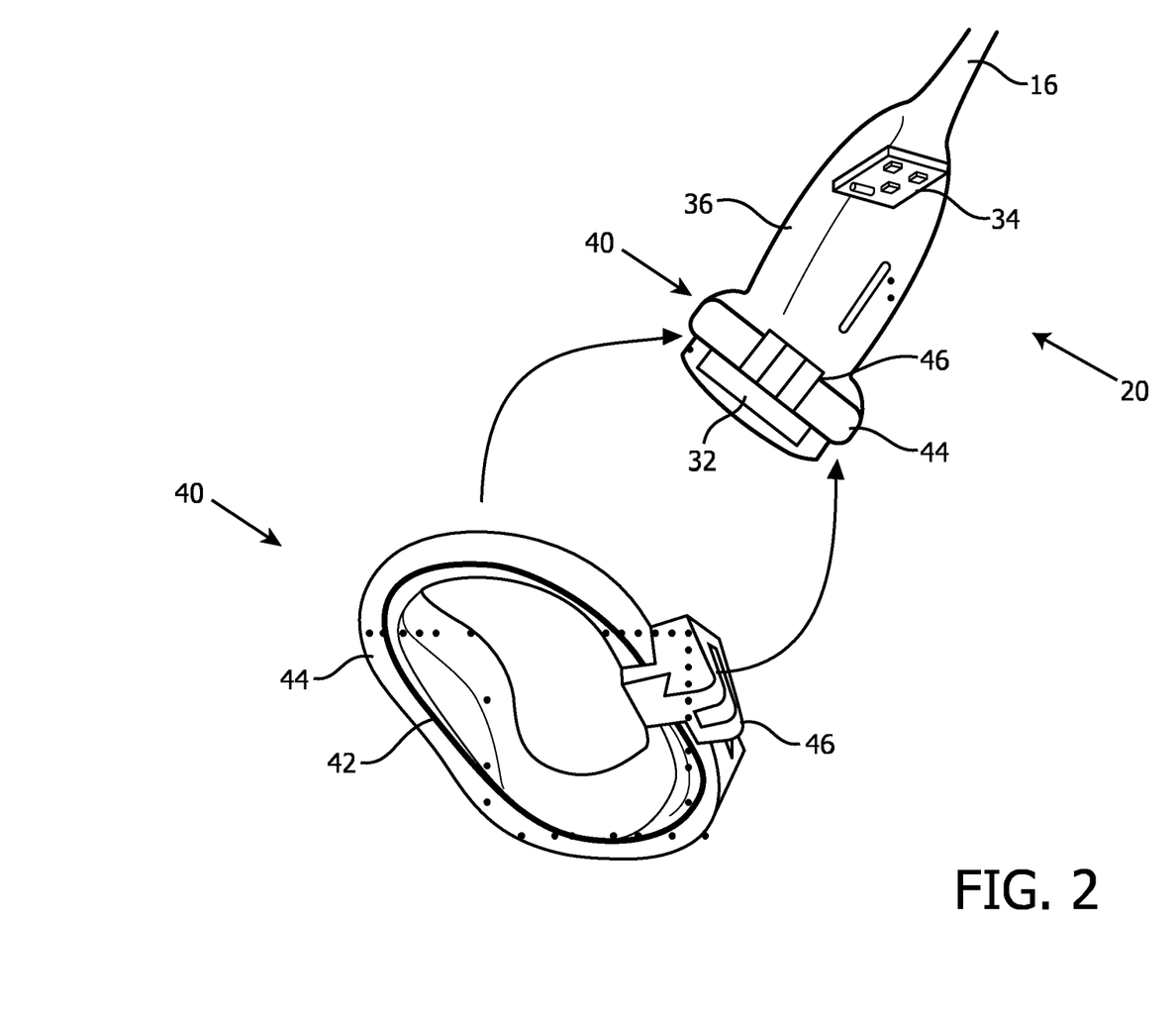
FIG. 2 diagrammatically shows an enlarged view of the ultrasound probe of the ultrasound device of FIG. 1, with a removable dosimeter for monitoring radiation dose received by the ultrasound probe. The dosimeter is shown both in its attached position in which it is attached to the ultrasound probe, and also removed from the ultrasound probe.

With continuing reference to FIG. 1 and with further reference to FIG. 2 (which shows an enlarged view of the US probe 20), the US probe 20 may include various components that are susceptible to radiation damage. Some principle internal components of the illustrative US probe 20 are shown diagrammatically, including an ultrasound transducer or transducer array 32 and an on-board electronic transducer driver 34. The ultrasound transducer or transducer array 32 may, for example, be a piezoelectric element or array of piezoelectric elements (e.g. single crystal elements or ceramic elements), or may be an array of micromachined ultrasound transducer (MUT) elements (e.g. capacitive MUT elements also called CMUT elements). Such ultrasound transducers can be susceptible to various modes of radiation damage, e.g. introduction of point defects impacting electrical performance, radiation-induced weakening of micromachined structural features, or so forth. The on-board electronic transducer driver 34, if present, may also be susceptible to radiation damage. Radiation damage susceptibility of the on-board electronic transducer driver 34 could in principle be reduced by employing radiation-hardened electronics however, using radiation-hardened electronics in the US probe 20 substantially increases manufacturing costs and may limit availability of certain electronic components. Moreover, even if the on-board electronic transducer driver 34 is constructed using entirely radiation-hardened electronics, the rated maximum permissible radiation exposure of these radiation-hardened electronic components may be exceeded in the case of direct exposure of the US probe 20 to the therapeutic radiation beam. It is noted that only selected illustrative components 32, 34 of the US probe 20 are shown more generally, the US probe 20 may include other components such as acoustic insulation, a backing block for the ultrasound transducer(s) 32, or so forth, which may also be susceptible to radiation damage via various potential modes such as modification of material resiliency properties due to radiation damage. In general, the various internal components 32, 34 of the US probe 20 are housed in an US probe housing 36.

With continuing reference to FIGS. 1 and 2, the ultrasound probe 20 includes an attached dosimeter 40 for use in monitoring the radiation dose received by the US probe 20. The illustrative dosimeter 40 is a removable component that can be detachably attached to the US probe 20—to illustrate this, FIG. 2 shows the dosimeter 40 attached to the US probe 20 and also in isolation, i.e. removed from the US probe 20. In other embodiments, the dosimeter may be permanently attached to the US probe, e.g. by adhesive, or may be integral with the US probe, e.g. disposed inside the housing 36 of the US probe. The illustrative dosimeter 40 comprises a thin-film active dosimeter device 42, e.g. a photoactive thin film amorphous silicon (a-Si) photocell or MOSFET that is sensitive to the ionizing radiation used in performing the radiation therapy. In a MOSFET design, oxide defects are introduced by radiation exposure, and the resulting change in MOSFET threshold voltage is associated to the cumulative radiation dose received. In a PIN design radiation defects are similarly introduced which changes the electrical characteristics (e.g. electrical resistance to forward diode current) of the PIN diode in a manner calibrated to the cumulative radiation dose. The PIN and MOSFET dosimeter designs are generally not resettable, since the radiation defects are not generally reversible. Thus, a PIN or MOSFET dosimeter is usually a one-time use design. However, the PIN or MOSFET dosimeter is readable in real-time since the change in forward current or threshold voltage can be measured by an electrical measurement circuit.

In another contemplated embodiment, the active dosimeter device 42 is a thermoluminescent dosimeter (TLD) device in which defects introduced into a crystalline material exhibit thermoluminescence upon heating. A TLD device has the advantage of being resettable (and hence reusable), as the heating applied during dose readout anneals the defects introduced by the radiation and returns the material to its original state. Other known dose-measuring devices may alternatively be used as the active dosimeter device 42.

In the illustrative dosimeter 40, the active dosimeter layer 42 is embedded in a structural collar 44 or sleeve that has a form factor comporting with a receiving groove of the US probe 20. For example, some existing transrectal US probes have a receiving groove for receiving a biopsy needle assembly, and this groove can be repurposed for mounting the illustrative dosimeter 40 without modifying the transrectal US probe. This is merely an illustrative mounting design, and other attachment mechanisms (e.g. adhesive, use of screws or other fasteners, or so forth) are also contemplated. Alternatively, the dosimeter can be permanently mounted inside the US probe housing 36.

With continuing reference to FIGS. 1 and 2, the illustrative dosimeter 40 further includes a data acquisition and wireless communication module 46 which includes readout electronics to measure the salient electrical characteristic (e.g. PIN diode forward resistance or MOSFET threshold voltage) of the PIN or MOSFET dosimeter layer 42 and (optionally) to convert the measured electrical characteristic to a dose value. The readout electronics 46 may include a wireless transmitter that transmits the dose data to a remote receiver 50 (see FIG. 1), or the transmitter may be a wired transmitter that transmits the dose data via a data line bundled into the US probe cable 16. An ultrasound probe dose analyzer 52, e.g. suitably implemented by programming of the computer 24, analyzes acquired by the dosimeter 40 to assess the cumulative dose received by the dosimeter 40 (and hence received by the US probe 20 to which the dosimeter 40 is attached or included within). If the data acquisition and wireless communication module 46 of the dosimeter 40 converts the measured electrical characteristic to dose then the analyzer 52 merely reads this value using the receiver 50 and time stamps the dose value; alternatively, the data acquisition and wireless communication module 46 may output the measured value of the electrical characteristic (e.g. PIN diode forward resistance or MOSFET threshold voltage) and the conversion to dose is performed at the analyzer 52. Optionally, the radiation exposure as a function of time is computed by the analyzer 52 as the time derivative of the measured dose. The dose and/or radiation exposure is compared with maximum permissible value thresholds, and if the thresholds are exceeded then some remedial action is taken.

The remedial action may, for example, include activating an alarm device 54 to output an alarm warning of the detection of excessive radiation dose or radiation exposure received by the ultrasound probe. In FIG. 1, the alarm device 54 is diagrammatically indicated. In some suitable implementations, the alarm device 54 may comprise a display 55 of the computer 24 programmed to display a warning of excessive dose (or excessive radiation exposure) to the US probe 20, optionally with some emphasis such as being displayed in red, flashing, or so forth, and optionally in conjunction with an audible alarm component output by a speaker of the computer 24.

Additionally or alternatively, the remedial action may include tagging ultrasound images acquired after the dose over-limit condition is detected with a warning that the US probe has received excessive radiation dose. In this way, the oncologist or other medical professional is informed of this condition so as to evaluate the US images accordingly.

Additionally or alternatively, in embodiments with the robot 28, the remedial action may include operate the US positioning controller 30 to control the robot 28 to reposition the US probe 20 further away from the ionizing radiation beam to reduce the radiation exposure of the US probe 20.

In embodiments that do not employ real-time readout, the data acquisition and communication module 46 may be omitted in favor of an external readout device, e.g. an illustrative dosimeter readout station 56, which includes a port 58 for connecting with the dosimeter and an electronic processor for processing the dosimeter data. In these embodiments, after the radiation therapy session (i.e. fraction) is completed, the dosimeter 40 is loaded into the port 58 of the dosimeter readout station 56 where the dose is read. If the dose is greater than a maximum permissible dose value threshold then the dosimeter readout station 56 outputs an alarm warning of the detection of excessive radiation dose received by the ultrasound probe 20. In some embodiments, the last dose reading for the dosimeter 40 is also stored, and the difference between the current dose reading and the last dose reading is taken as the average radiation exposure received by the US probe 20 during the last radiation therapy session. If this (average) radiation exposure exceeds a maximum permissible value threshold then the dosimeter readout station 56 outputs an alarm warning of the detection of excessive radiation exposure received by the ultrasound probe 20. As with the warning device 54, the mode of the warning can vary—the dosimeter readout station 56 may include a display 59 showing the measured dose and the threshold, and/or an audible alarm may sound, or so forth. Note that the dosimeter readout station 56 may be set up to read the dosimeter 40 after removal from the US probe 20 or, if the dosimeter is integral with the US probe, then the combined unit may be loaded into the port 58 of the dosimeter readout station. In this latter case the US probe housing preferably includes an electrical connection point providing access to connect with the port 58 of the dosimeter reading device 56 to read the dosimeter. In general, the port or connector 58 can take any form capable of transmitting the dose or radiation exposure data. For example, the connector 58 may be a device-specific connector or a digital connector such as a USB or micro-USB connector if the dosimeter 40 includes digitizing electronics and a mating USB or micro-USB connector.

As previously noted, the dosimeter may optionally be replaced by an ionizing radiation detector configured to detect the ionizing radiation used in the radiation therapy. In these embodiments the detector output is a current radiation exposure value, and the radiation dose is suitably computed by time integration of the radiation exposure values.

Figure 3:
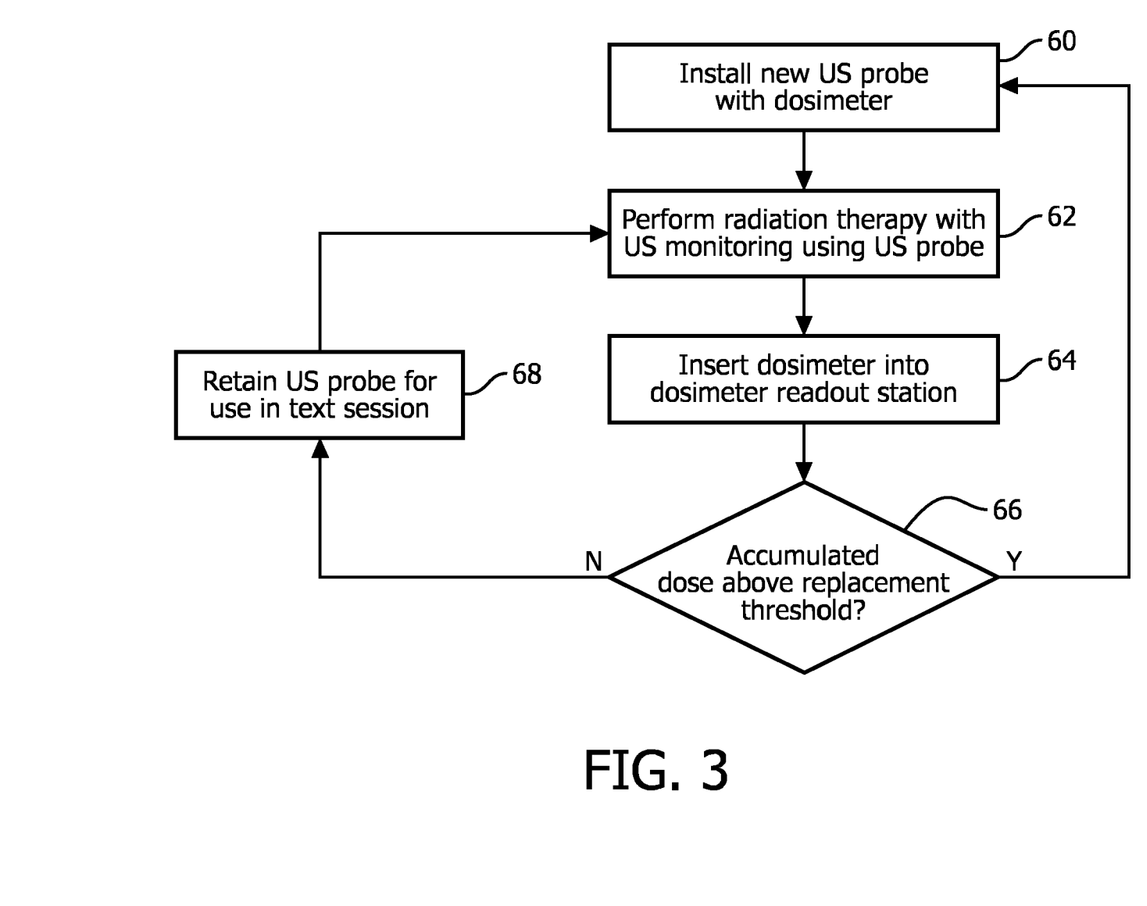
FIG. 3 diagrammatically shows a maintenance method for monitoring cumulative radiation dose received by the ultrasound probe of FIGS. 1 and 2.

With reference to FIG. 3, an illustrative process is described which uses the dosimeter readout station 56 to monitor radiation dose received by the US probe 20 for maintenance purposes. In an operation 60, a new ultrasound probe is installed together with its attached or integral dosimeter. If the dosimeter is not resettable then a new dosimeter should be used. If the dosimeter is resettable then optionally it may be a previously used dosimeter that has been reset, e.g. by sufficient heating in the case of a dosimeter of the TLD type. In an operation 62, a radiation therapy session (i.e. fraction in the case of a fractionated radiation therapy regimen) is performed using the US probe in providing US imaging to monitor the patient during the therapy session. In an operation 64 performed after completion of the radiation therapy session, the dosimeter is inserted into the dosimeter readout station 56 (either after removal from the US probe 20 or as a unit together with the US probe). The dosimeter readout station 56 outputs the accumulated radiation dose received by the US probe, and in an operation 66 it is decided whether the accumulated dose is greater than the maximum dose above which the US probe 20 should be replaced. If so, then process flow returns to operation 60 to install a new US probe (and the old US probe is disposed of in accordance with applicable governmental and/or medical institutional guidelines). If, on the other hand, in the operation 66 it is determined that the accumulated dose has not yet reached the maximum dose at which the US probe is to be replaced, then process flow progresses to operation 68 to retain the current US probe 20 for use in a next radiation therapy session as per operation 62. It will be noted that in the embodiment of FIG. 3 the data acquisition and wireless communication module 46 may be omitted from the dosimeter 40.

Figure 4:
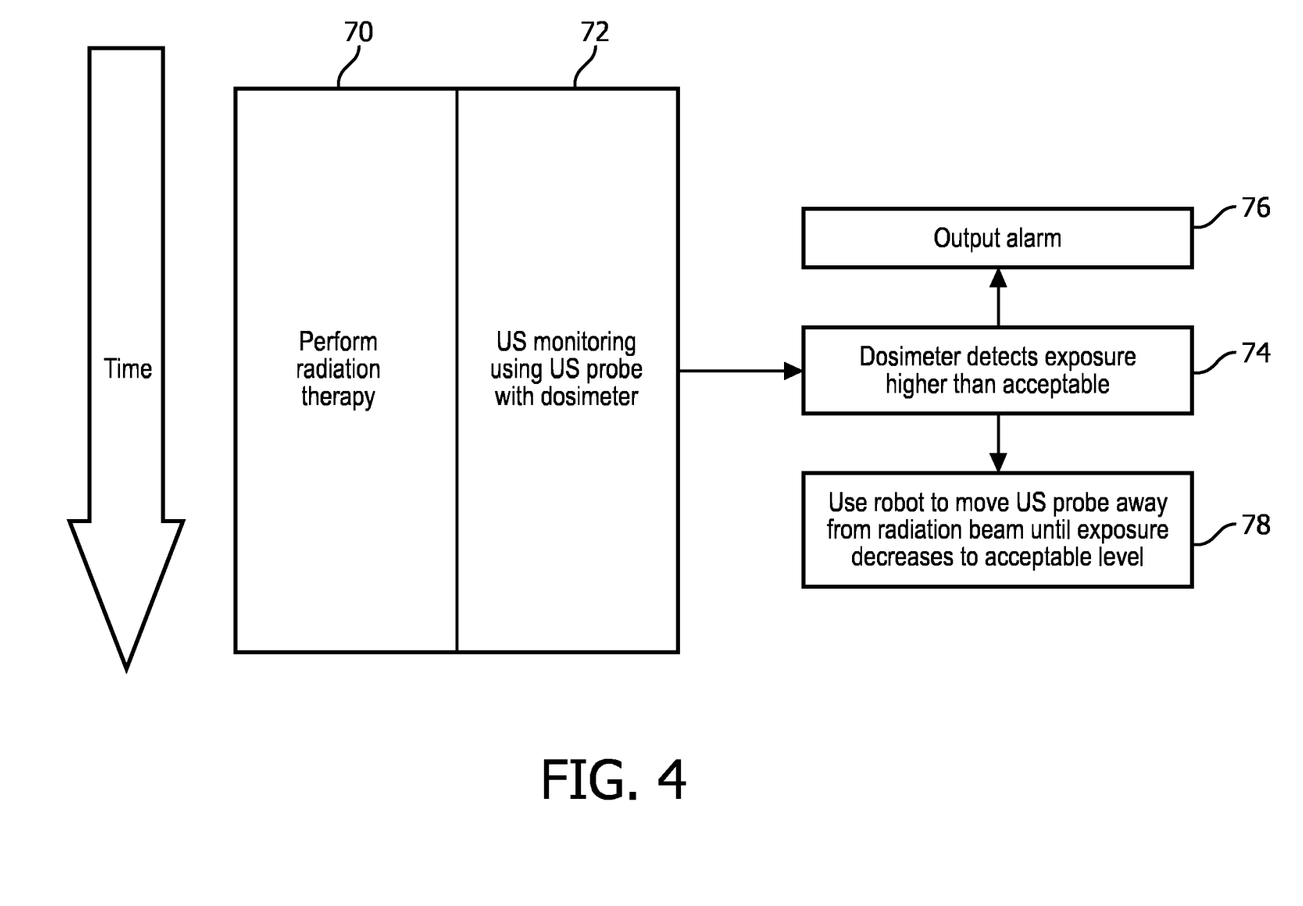
FIG. 4 diagrammatically shows a method for monitoring radiation exposure received by the ultrasound probe of FIGS. 1 and 2 and taking remedial action in the event this exposure exceeds an acceptable level.

With reference to FIG. 4, an illustrative process is described which uses the dosimeter 40 for real-time monitoring of dose and/or radiation exposure. In an operation 70 a radiation therapy session (fraction) is performed. Concurrently with the operation 70, an US monitoring operation 72 is performed using the US probe 20 with its dosimeter 40. If, at some point in time the dosimeter 40 and associated processor 24, 52 detects radiation exposure higher than an acceptable level (operation 74) then remedial action is taken, such as outputting an alarm (operation 76) and/or operating the robot 28 to move the US probe 20 away from the radiation beam until the radiation exposure decreases to an acceptable level (operation 78). As noted previously, in the operation 74 the radiation exposure is suitably determined as the time derivative of the accumulated dose (unless an ionizing radiation detector is used in place of the dosimeter 40, in which case the detector directly measures radiation exposure level). This embodiment employs the data acquisition and wireless communication module 46 to offload current dose measurements as a function of time from the dosimeter 40.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An ultrasound probe comprising:
   an ultrasound probe housing;
   one or more ultrasound transducers disposed in the ultrasound probe housing;
   a dosimeter or ionizing radiation detector disposed in or attached to the ultrasound probe housing; and
   a monitoring device configured to receive radiation dose or radiation exposure data acquired by the dosimeter or ionizing radiation detector and including an electronic processor programmed to (i) detect excessive radiation dose or radiation exposure received by the ultrasound probe based on the radiation dose or radiation exposure data acquired by the dosimeter or ionizing radiation detector and (ii) output an alarm warning of the detection of excessive radiation dose or radiation exposure received by the ultrasound probe.

2. The ultrasound probe of claim 1 wherein the monitoring device comprises a display and the electronic processor is programmed to (ii) output the alarm comprising a message displayed on the display warning of the detection of excessive radiation dose or radiation exposure received by the ultrasound probe.

3. The ultrasound probe of claim 1 further comprising:
   a robot connected to position the ultrasound probe or ionizing radiation detector;
   wherein the electronic processor is further programmed to (iii) operate the robot to move the ultrasound probe in response to the detection of excessive radiation dose or radiation exposure received by the ultrasound probe.

4. The ultrasound probe of claim 1 further comprising:
   a transmitter;
   wherein the monitoring device includes a receiver configured to connect with the transmitter to receive the radiation dose or radiation exposure data acquired by the dosimeter or ionizing radiation detector.

5. The ultrasound probe of claim 1 wherein the monitoring device includes a connector configured to connect with the dosimeter or ionizing radiation detector to receive the radiation dose or radiation exposure data acquired by the dosimeter or ionizing radiation detector.

6. The ultrasound probe of claim 1 wherein the dosimeter or ionizing radiation detector comprises a dosimeter.

7. The ultrasound probe of claim 6 wherein the dosimeter is a one-time use dosimeter that is not resettable.

8. The ultrasound probe of claim 7 further comprising:
   an electronic transducer driver disposed in the ultrasound probe housing and operatively connected to drive the one or more ultrasound transducers;
   wherein the electronic transducer driver is not radiation hardened.

9. The ultrasound probe of claim 1 wherein:

the dosimeter or ionizing radiation detector comprises a dosimeter configured to acquire radiation dose data; and the electronic processor is programmed to (i) detect excessive radiation exposure received by the ultrasound probe by computing radiation exposure from a time derivative of the radiation dose data or estimating average radiation exposure from a dose difference between successive dose measurements of the radiation dose data.

10. The ultrasound probe of claim 1 wherein the one or more ultrasound transducers comprise one or more piezoelectric ultrasonic transducer elements or an array of micromachined ultrasonic transducer (MUT) elements.

11. An external beam radiation therapy device comprising:

a radiation therapy delivery device configured to apply an ionizing radiation beam to a subject; and an ultrasound probe as set forth in claim 1 configured to monitor an internal organ of the subject while the radiation therapy delivery device applies the ionizing radiation beam to the subject.

12. The external beam radiation therapy device of claim 11 wherein the monitoring device is not configured to measure radiation dose or radiation exposure delivered to the subject by the radiation therapy delivery device.

13. The external beam radiation therapy device of claim 11 wherein the radiation therapy delivery device is configured to apply an ionizing x-ray, electron, or proton beam to the subject.

14. An ultrasound probe comprising:

an ultrasound probe housing;

one or more ultrasound transducers disposed in the ultrasound probe housing; and a one-time use dosimeter that is not resettable disposed in or attached to the ultrasound probe housing and is configured to detect excessive radiation dose or radiation exposure received by the ultrasound probe.

* * * * *